United States Patent
Reed et al.

(10) Patent No.: US 6,807,849 B1
(45) Date of Patent: Oct. 26, 2004

(54) FOAM GENERATOR AND VISCOMETER APPARATUS AND PROCESS

(75) Inventors: Troy D. Reed, Stillwater, OK (US); Mark B. Pickell, Tulsa, OK (US); Leonard J. Volk, Tulsa, OK (US)

(73) Assignee: The University of Tulsa, Tulsa, OK (US)

( * ) Notice: Subject to any disclaimer, the term of this patent is extended or adjusted under 35 U.S.C. 154(b) by 0 days.

(21) Appl. No.: 10/282,151

(22) Filed: Oct. 28, 2002

(51) Int. Cl.$^7$ .............................................. G01N 37/00
(52) U.S. Cl. ................................... 73/60.11; 73/54.28
(58) Field of Search ......................... 73/54.01, 54.28, 73/54.43, 60.11; 166/292, 608.6, 309

(56) References Cited

U.S. PATENT DOCUMENTS

| | | | |
|---|---|---|---|
| 1,817,739 A | | 8/1931 | Dintilhac |
| 2,027,903 A | | 1/1936 | Dintilhac ........................ 73/51 |
| 3,435,666 A | | 4/1969 | Fann .............................. 73/60 |
| 3,452,726 A | * | 7/1969 | Symanski ..................... 123/260 |
| 4,077,251 A | | 3/1978 | Winter ........................... 73/59 |
| 4,085,521 A | * | 4/1978 | Neuroth .......................... 34/89 |
| 4,403,502 A | * | 9/1983 | Lindt ......................... 73/54.09 |
| 4,526,907 A | * | 7/1985 | Thiele et al. ................ 521/133 |
| 4,534,427 A | * | 8/1985 | Wang et al. .................... 175/67 |
| 4,544,489 A | * | 10/1985 | Campbell et al. ............ 210/709 |
| 4,620,983 A | * | 11/1986 | Zimmer ......................... 427/8 |
| 4,621,521 A | * | 11/1986 | Lattek et al. ............... 73/60.11 |
| 4,717,582 A | * | 1/1988 | Kotoye et al. .................. 427/8 |
| 5,056,034 A | * | 10/1991 | Rucki et al. ................... 702/46 |
| 5,154,088 A | * | 10/1992 | Lehnert et al. ................ 73/866 |
| 5,301,541 A | * | 4/1994 | Joseph et al. ............... 73/54.32 |
| 5,306,734 A | | 4/1994 | Bass et al. ..................... 521/63 |
| 5,321,974 A | * | 6/1994 | Hemmings et al. ......... 73/54.31 |
| 5,365,777 A | | 11/1994 | Layton .......................... 73/54 |
| 5,372,789 A | * | 12/1994 | Lamberts et al. ............ 422/133 |
| 5,394,738 A | | 3/1995 | Bass et al. ..................... 73/54 |
| 5,403,088 A | * | 4/1995 | Killmer et al. ............. 366/102 |
| 5,454,986 A | * | 10/1995 | Lessen ......................... 261/93 |
| 5,645,011 A | * | 7/1997 | Winkler et al. ............. 116/264 |
| 5,708,197 A | * | 1/1998 | Todd et al. ................ 73/54.28 |
| 5,770,795 A | * | 6/1998 | Behar et al. ............... 73/54.23 |
| 6,182,503 B1 | * | 2/2001 | Mode et al. ............... 73/54.04 |
| 6,240,770 B1 | * | 6/2001 | Raffer ....................... 73/54.28 |
| 6,260,413 B1 | | 7/2001 | Charron ....................... 73/147 |
| 2003/0054957 A1 | * | 3/2003 | Irvin et al. ................... 502/416 |

FOREIGN PATENT DOCUMENTS

DE          4236150 A1  *  4/1994   ............. F16F/9/44

* cited by examiner

Primary Examiner—Hezron Williams
Assistant Examiner—John Fitzgerald
(74) Attorney, Agent, or Firm—Head, Johnson & Kachigian

(57) ABSTRACT

An apparatus and process to generate a liquid-gas-surfactant foam and to measure its viscosity and enable optical and or electronic measurements of physical properties. The process includes the steps of pumping selected and measured liquids and measured gases into a mixing cell. The mixing cell is pressurized to a desired pressure and maintained at a desired pressure. Liquids and gas are mixed in the mixing cell to produce a foam of desired consistency. The temperature of the foam in the mixing cell is controlled. Foam is delivered from the mixing cell through a viscometer under controlled pressure and temperature conditions where the viscous and physical properties of the foam are measured and observed.

20 Claims, 6 Drawing Sheets

FOAM GENERATOR AND VISCOMETER APPARATUS AND PROCESS

STATEMENT REGARDING FEDERALLY SPONSORED RESEARCH OR DEVELOPMENT

This invention was made with U.S. Government support under DOE Grant DE FG26-99BC15178 awarded by the United States Department of Energy. The U.S. Government has certain rights in the inventions

BACKGROUND OF THE INVENTION

1. Field of the Invention

The present invention is directed to an apparatus and process to generate a foam under controlled conditions, measure its viscosity and facilitate measurements of its physical properties. In particular, the present invention is directed to a foam generator and viscometer apparatus and a process which is capable of controlling multiple variables during the generation of a foam and allowing the foam to flow under controlled conditions in order to maintain constant foam properties while being measured.

2. Prior Art

A number of industries, such as the petroleum drilling and production industry use foams for a wide range of tasks. For example, foams are utilized in the petroleum industry for: drilling underbalanced wells, the transport of proppants during fracturing of wells to improve production, to enhance oil recovery from partially depleted reservoirs, and for environmental remediation of underground water. In the case of drilling new wells into low-pressure reservoirs, conventional drilling muds are too heavy and can overpressurize the porous rock formations and cause "skin damage" that reduces the flow of either crude and/or gas from the well. This problem is avoided by using lighter weight drilling fluids such as foams.

In petroleum applications, foam is produced on-site at a drilling and/or production location. The various components of the foam such as liquids and gases are mixed together and then pumped downhole. Accordingly, it is important to know the properties of the foam and to control its characteristics.

Additional applications would be in the chemical and pharmaceutical industries.

A study of foam properties includes measurements of its viscous properties and its physical properties such as foam texture, which includes bubble size, size distribution, and bubble shape. All instrument that can produce foam under controlled conditions and measure its properties will provide valuable engineering data that can be used in a variety of industries.

There have been proposals in the past to study foams and similar liquids. The Bass Patents (U.S. Pat. Nos. 5,306,734 and 5,394,738) disclose a device to study emulsions which includes a fixed volume mixing chamber and conventional flow meters to measure feed rates of oil and water into the mixing chamber. Bass measures viscosity of samples of the emulsion at ambient temperature and atmospheric pressure.

Joseph (U.S. Pat. No. 5,301,541) discloses a device and a method for drag determination having a rib surface 20 attached to an inner block 14 and a rib surface 22 attached to a housing 12.

There remains a need for an instrument and a process to generate a foam and measure its physical and viscous properties. The device should be capable of controlling a number of variables independently, such as foam quality (ratio of gas to total fluid volume), pressure, temperature, surfactants and other additives, bubble size and surface roughness.

SUMMARY OF THE INVENTION

The present invention produces a liquid-gas-surfactant foam by selectively mixing components of various ratios and controlling the resulting bubble size by adjusting the amount of mixing or shear energy applied. It also conveys the foam, at constant pressure and temperature, through a viscometer, and enables optical measurements of the foam's physical properties.

Gas, contained under pressure in a cylinder, is dispensed and delivered through fluid lines. Liquids, including surfactants and additives, are initially premixed in a volume-calibrated container and then introduced via a pump into a mixing cell. Once the desired volume of liquids has been delivered into the mixing cell, pressurized gas is then allowed to flow into the mixing cell, thereby adding a volume of gas to the liquid volume. As the combined volume of liquid and gas increases inside the mixing cell, a piston begins to rise from its resting place upon a stop or stops.

Generation of foam is initiated by rotating a propeller driven by a shaft that is rotated by a variable speed motor. Flow within the mixing cell is forced upward in the center of the mixing chamber and thereafter is diverted downward along the sides of the mixing cell by a specially contoured piston.

Additional mixing of the foam can be achieved by optionally drawing liquids, gas and foam from either the top or bottom of the mixing cell with a pump and circulating back to the opposite end of the mixing cell.

After a satisfactory foam has been generated, valves may be manipulated to direct gas pressure to the top of the piston, thereby forcing a smooth continuous flow of foam from the mixing cell through a viscometer. The rate at which foam flows from the mixing cell may be measured by a linear voltage differential transformer. Foam from the mixing cell enters a fluid line and passes into a Couette-type viscometer having interchangeable elements (stationary cup and a rotor or a rotating sleeve and a stationary bob) with different values of surface roughness. This feature enables studies of the effects of surface roughness on "wall slip" of foams at a solid surface. Fluid flow is controlled by a metering valve located downstream of the viscometer that allows flow rate to be controlled by varying the opening of the valve. The physical properties of a foam may be visually and electronically assessed at four view ports. Two are located near the Generator, and two others are located on the entry and exit sides of the Viscometer.

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

Figure 1:
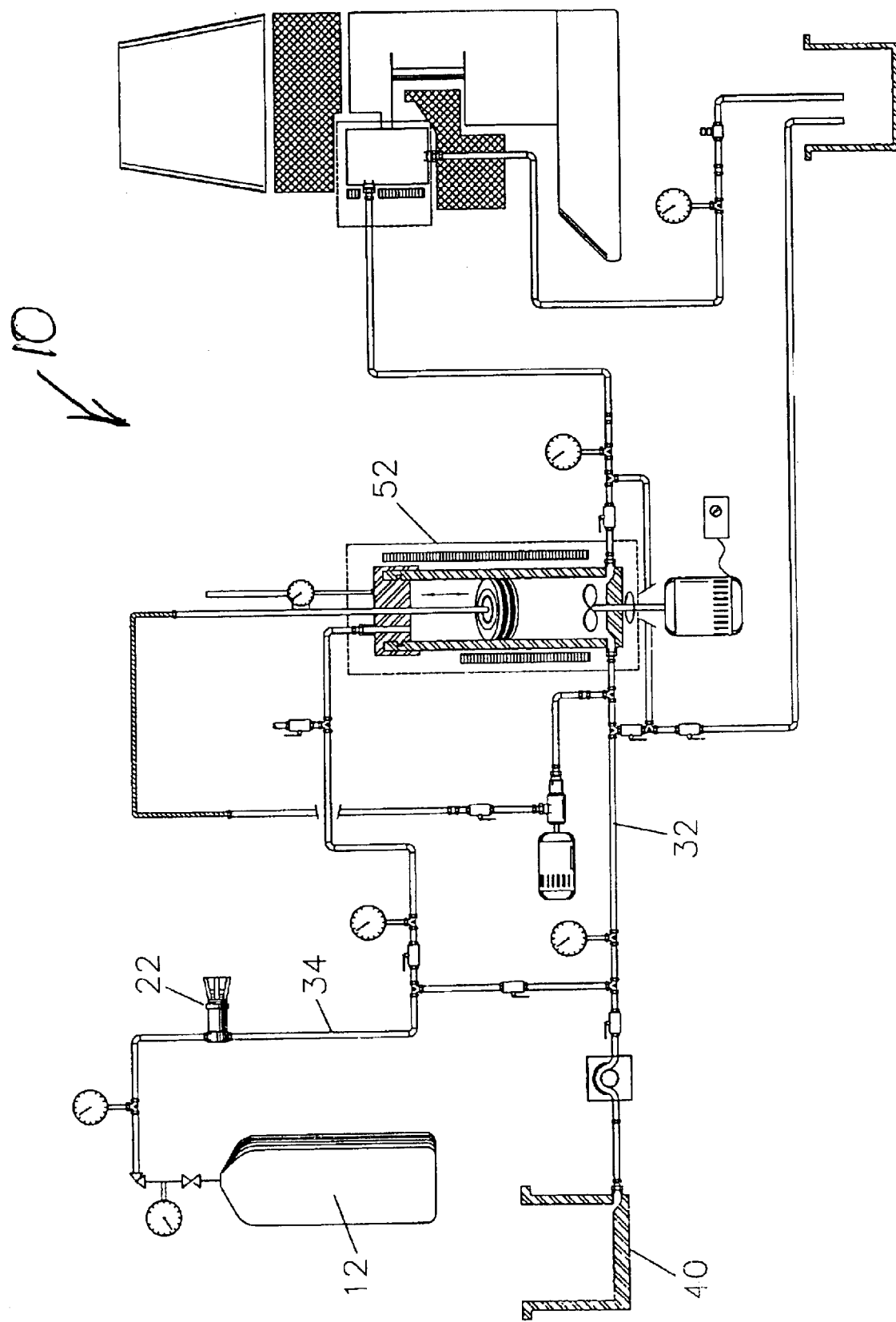
FIG. 1 is an overall schematic diagram of a foam generator and viscometer apparatus constructed in accordance with the present invention.
Figure 2:
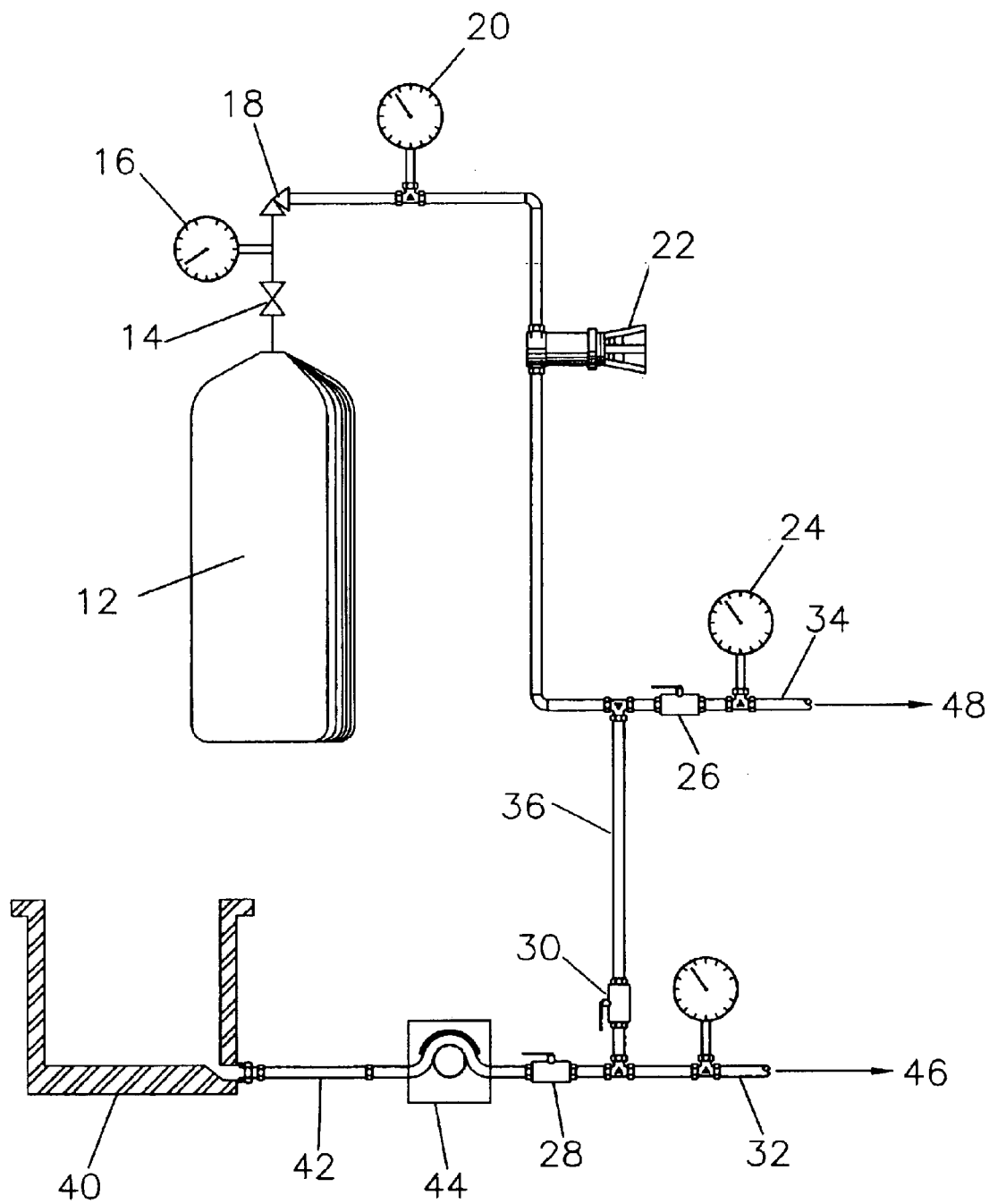
FIGS. 2, 3 and 4 provide additional details about three separate sections of the apparatus shown in FIG. 1 for ease of comprehension.
Figure 3:
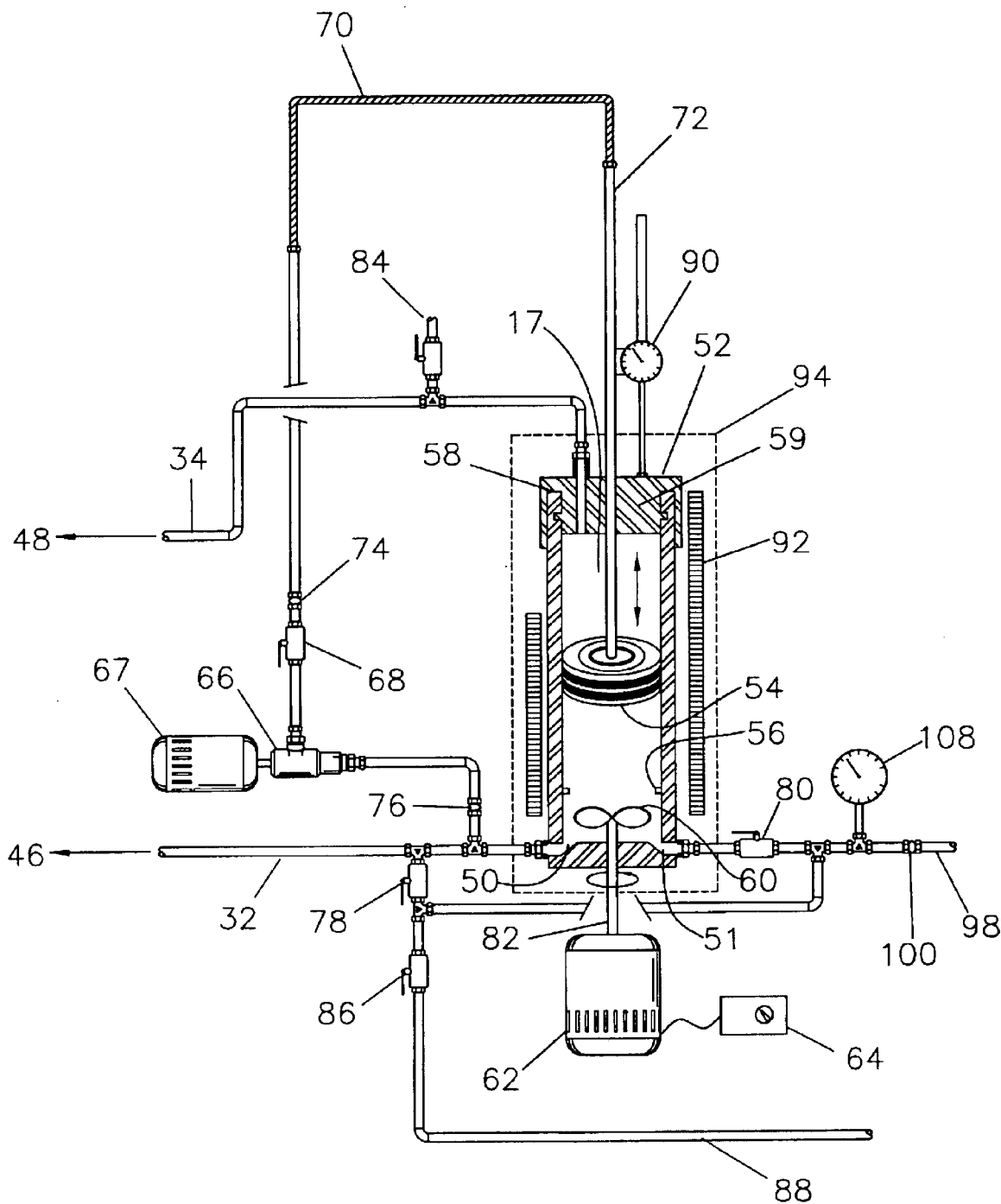
Figure 4:
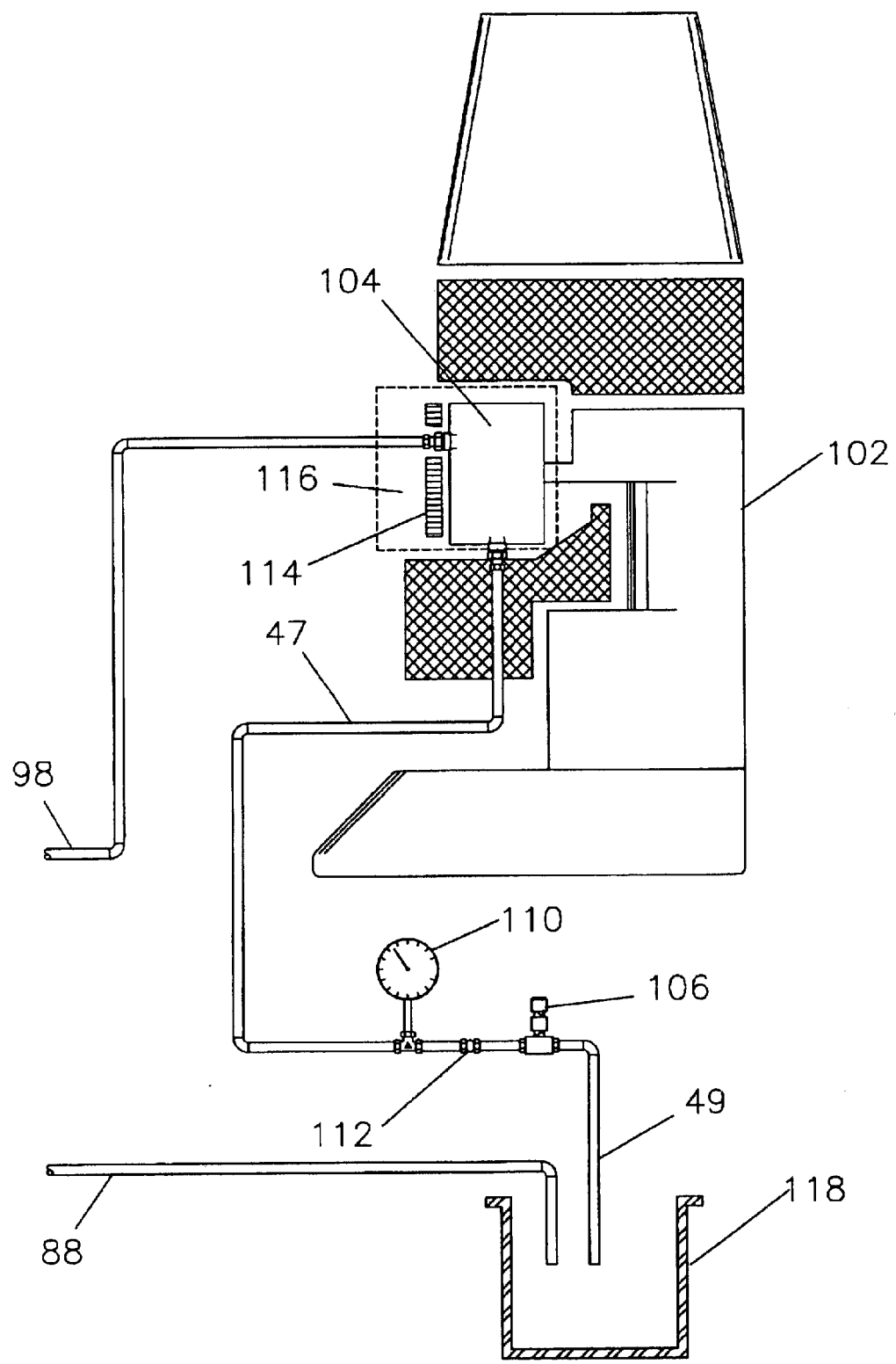

FIG. 1 is an overall schematic diagram of the foam generator and viscometer apparatus 10 and process of the present invention. The process includes a mechanism to produce a liquid-gas-surfactant foam by selectively mixing components in various ratios, varying the resulting bubble size by adjusting the amount of mixing or shear energy applied, and measuring the resulting rheological properties and enables optical measurements of the physical properties. As will be described herein, the temperature and the pressure are controlled throughout the entire process. The overall apparatus 10 is illustrated in FIG. 1. FIGS. 2, 3 and 4 divide the overall apparatus and process into three sections for ease of comprehension.

FIG. 2 illustrates the initial portion of the process that deals with dispensing the constituent gases and fluids at the beginning of the process. Gas, contained under pressure in a cylinder 12, may be dispensed and delivered through a tank valve 14 and a pressure regulator 18. Nitrogen would be an example of a gas suitable for the present invention although air and other gases may also be used. Pressure inside the gas cylinder 12, upstream of a pressure regulator 18 will be indicated on pressure gauge 16. Pressure downstream of the pressure regulator 18 will be indicated and observed on pressure gauge 20. A pressure regulator 22 may further refine the precise pressure of gas introduced. The final line pressure is measured by a high precision pressure gauge 24.

A pair of fluid lines 32 and 34 are interconnected by fluid line 36. By manipulation of valves 26, 28 and/or 30, gas may be dispensed through either line 32 or 34.

Liquids, including surfactants and additives, are initially premixed in a volume-calibrated container 40 and then introduced through low-pressure flexible tubing 42 in fluid communication with pump 44. The pump 44 controls the volume of liquids introduced. In the sequence of operations, the liquids from container 10 are premixed and dispensed into the mixing cell first. Thereafter, gas from the high-pressure gas container 12 is introduced. Arrows 46 and 48 in FIG. 2 illustrate the flow of fluids and the connection with lines 32 and 34, respectively, in FIG. 1.

FIG. 3 primarily pertains to generation of the foam. Liquids are dispensed through line 32 and through a port 50 into a fluid tight mixing cell 52. As the volume of liquid increases inside of the mixing cell 52, a piston 54 begins to rise from its resting place upon a stop or stops 56. A portion of the mixing cell 52 above the movable piston 54 is assigned reference numeral 17. A port to vent high-pressure and high-temperature foam to the viscometer 102 is designated as reference numeral 51.

Once a desired volume of liquids has been delivered into the mixing cell 52, valves 26, 30, and 28 (as shown in FIG. 2) may be manipulated to allow pressurized gas to flow through line 32 thereby adding a volume of gas to the liquid volume in the mixing cell. The piston 54 may be raised to its maximum height within the mixing cell against a cap 58 at the top of the mixing cell. Both the liquids and gas introduced inside the mixing cell are at a selected pressure. The fluids in the mixing cell are then heated to the desired temperature. Seals 59 assist in maintaining a fluid-tight seal between the cap and the mixing cell.

Figure 5:
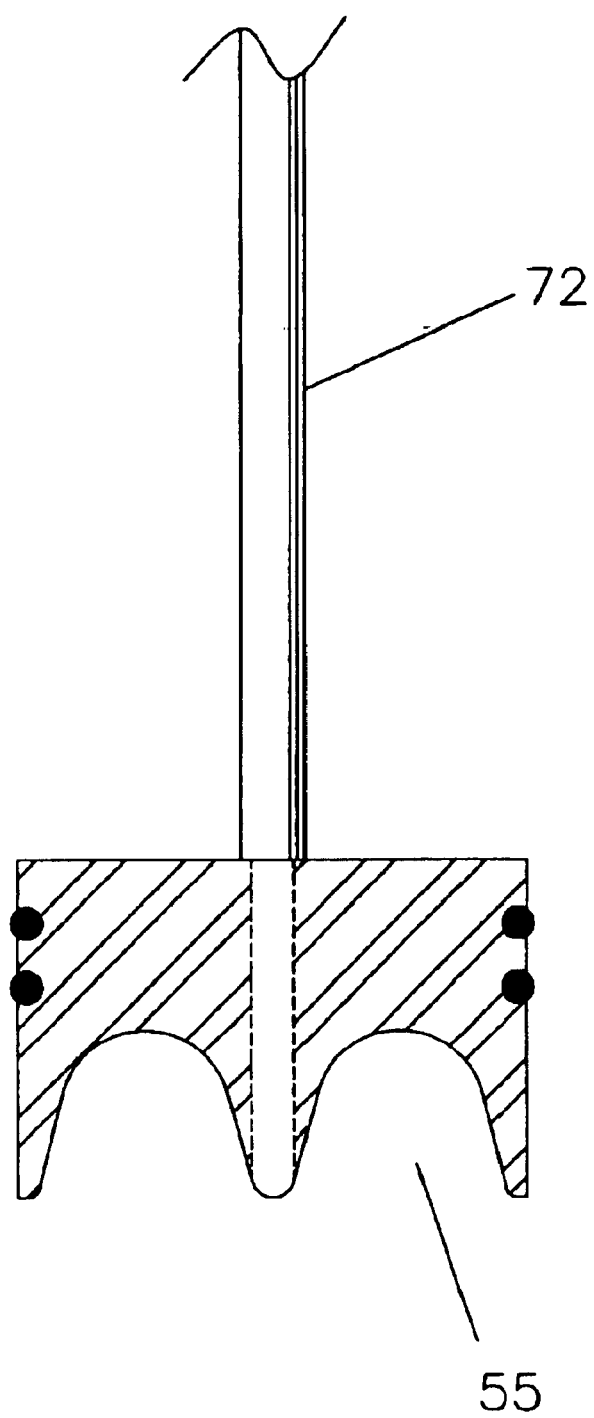
FIG. 5 illustrates a sectional view of a piston utilized in connection with a mixing cell of the present invention.

Generation of foam is initiated by rotating a propeller 60 driven by A shaft 82 that is rotated by a variable speed motor 62 or other mechanism. A control 64 can be used to control the speed of rotation of the propeller 60. Flow within the mixing cell is forced upward in the center of the mixing chamber as the propeller picks up and moves liquids, gases and foam from the bottom and propels them upward. The flow encounters the piston and is thereafter diverted downward along the sides of the mixing cell. This recirculation is facilitated by a contoured piston having recessed portions 55 as shown in the partial section view of FIG. 5.

Bubble size can be controlled by varying propeller rotary speed and by selection of propeller design configurations.

Additional mixing of the foam can be achieved by optionally drawing liquids, gas and foam from either the top or bottom of the mixing cell with a pump 66 and circulating back to the opposite end of the mixing cell 52. In one direction, the flow would move through entry port 50, pump 66 (driven by motor 67), valve 68, flexible hose 70 and a hollow shaft 72 of the piston 54. Characteristics of the foam, such as bubble size and gas-liquid ratio may be visually and/or electronically assessed at view ports 74 and 76.

After a satisfactory foam has been generated, valves 78, 80, and 26 (shown in FIG. 2) may be manipulated to direct gas pressure to the top of the piston 54 and into line 98. After pressurizing line 98, which connects the mixing cell with a viscometer to be discussed, and manipulating valve 106, a smooth continuous flow of the foam sample is accomplished.

As shown in FIG. 3, the apparatus also includes a vent valve 84, a drain valve 86 and a drain line 88.

A mechanism may be provided to measure movement of the piston 72 such as a linear voltage differential transformer 90 which can be used to measure piston position and rate-of-travel which provides a measure of flow rate of foam from the mixing cell 52.

The apparatus may also include a mechanism to increase and maintain the temperature inside the mixing cell, such as electrical heater 92, with thermal insulation (indicated by dashed lines 94).

An alternate configuration of the mixing cell includes, an optional propeller shroud 96 (shown in FIG. 6) which is designed to promote and enhance mixing.

Foam exits the mixing cell through fluid line 98. A view port 100 is provided in line 98 that allows visual and optical measurements of the foam prior to entering the viscometer.

FIG. 4 illustrates the apparatus downstream of the mixing cell 52 and includes a viscometer 102. Foam from the mixing cell enters fluid line 98 and passes into a viscometer cup 104. Foam can flow as needed, during the viscometer measurement process, in order to compensate for any foam degradation caused by drainage (syneresis) and/or bubble coalescence. Foam flow is controlled by a micrometer valve 106 located downstream of the viscometer which allows flow rate to be controlled by varying the opening of the valve. Pressure is monitored by pressure gauges 110 and 108 (shown in FIG. 3) and is controlled by maintaining a specified gas pressure above the piston 54 of the mixing cell 52. A portion 2 of the exhaust 2 flow line located between the viscometer 102 and the pressure gauge 112 is designated reference numeral 47 in FIG. 4. A portion of this exhaust line between the needle valve 106 and the waste tank 118 is designated as reference numeral 49.

A view port is located on each side of the viscometer 102 in order to evaluate and compare properties of the foam before and after passing through the viscometer. The foam may be visually and electronically assessed at view port 112, downstream of the viscometer, for comparisons with the properties, of the foam as it passes through view port 100 (FIG. 3) and immediately prior to entering the viscometer 102.

The foregoing arrangement provides a method to control flow of foam through the apparatus.

In a preferred embodiment of the present invention, a modified Couette-type rotary viscometer is employed with either a rotor inside a stationary cup or a stationary bob with an outer rotating sleeve. The internal surfaces of these elements are modified to have a variety of surface roughnesses so the effects of changing wall roughness on foam rheological measurements can be systematically investigated.

The viscometer 102 includes a heater 114 that enables control and selection of temperature and thermal insulation (indicated by a dashed surrounding block 116) to maintain a uniform temperature inside the viscometer cup 104. A drain receptacle 118 will receive waste from line 49 exiting the viscometer and from line 88 exiting the mixing cell or any exhausts from containers 12 and 40.

Figure 6:
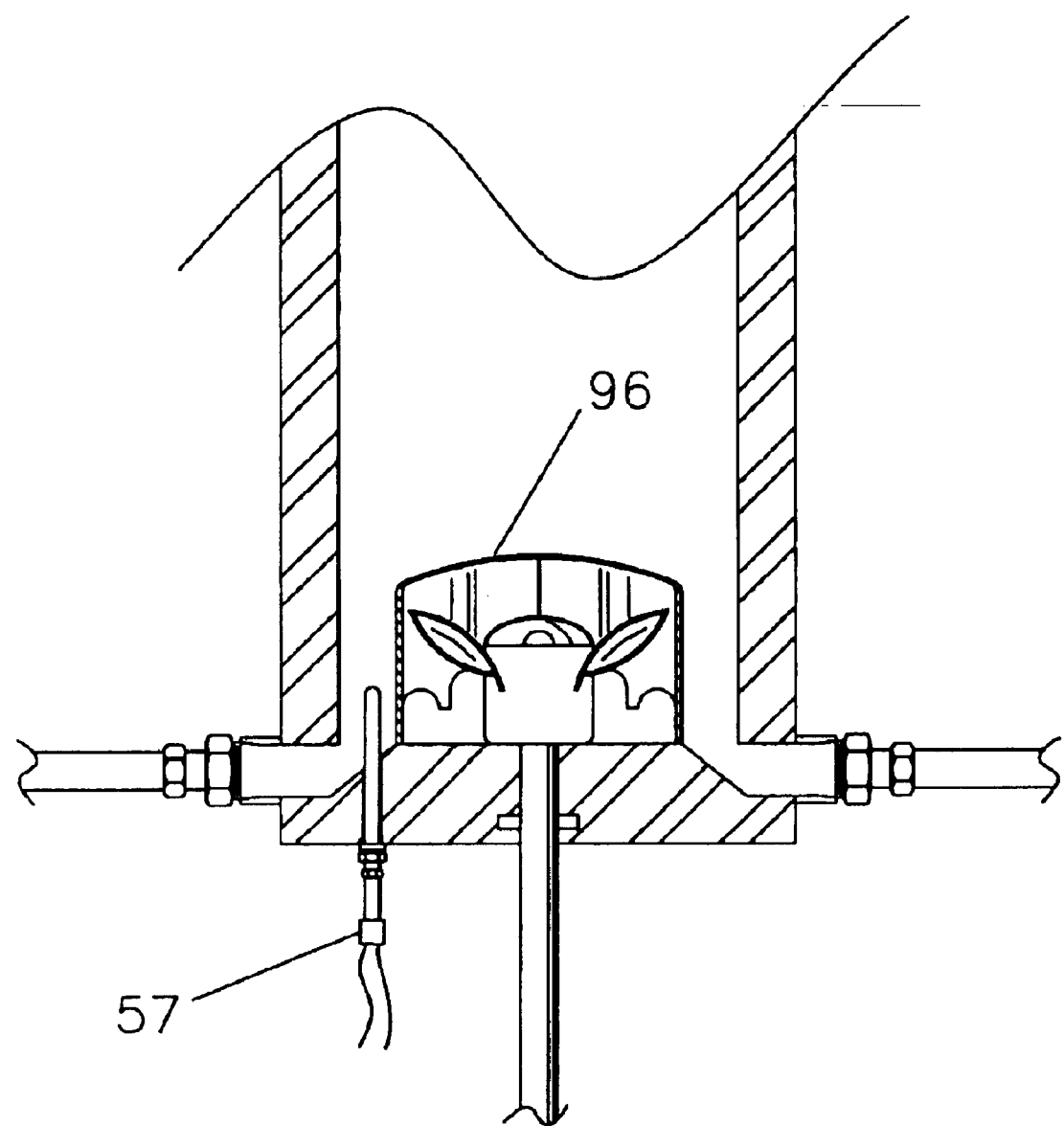
FIG. 6 illustrates an alternate mixing cell having a propeller with a shroud to assist in mixing of components within the mixing cell.

An alternate mechanism may be used to control the rate-of-flow through the viscometer cup. Instead of flowing fluid directly into the drain receptacle 118, flow may be directed into a pressurized container of such size that all of the liquid and gas components of the foam are contained therein. Flow is then controlled through micrometer valve 106 which would be located on the top of the pressurized container and be used to control flow by allowing only the gaseous phase to be vented. This arrangement permits better control of flow rate rather than having an intermittent flow of liquid and gas passing through the micrometer valve 106. FIG. 6 illustrates two additional features of the mixing cell. A temperature sensor 57 used to control heating elements 92 and achieve a desired temperature is provided. A shroud 96 surrounds a propeller/impeller is designed to promote better circulation of fluids between the bottom and top of the closed volume within the mixing cell 52.

Whereas, the present invention has been described in relation to the drawings attached hereto, it should be understood that other and further modifications, apart from those shown or suggested herein, may be made within the spirit and scope of this invention.

What is claimed is:

1. A process to generate a liquid-gas-surfactant foam and measure its properties, which process comprises:

delivering selected and measured liquids and gases into a fluid-tight mixing cell;

pressurizing said mixing cell to a desired pressure and maintaining at a desired pressure;

mixing said liquids and gases in said mixing cell to produce a foam of desired consistency, characteristics and quality;

controlling temperature of said fluids in said mixing cell;

delivering said foam from said mixing cell to a viscometer; and measuring properties of said foam while by passing said foam through said viscometer.

2. A process to generate a liquid-gas-surfactant foam as set forth in claim wherein the steps of pressurizing said mixing cell, mixing said fluids, and controlling temperature may be performed in any order.

3. A process to generate a liquid-gas-surfactant foam as set forth in claim including the additional step of measuring flow rate of said foam delivered from said mixing cell to said viscometer.

4. A process to generate a liquid-gas-surfactant foam as set forth in claim 3 wherein said step of measuring flow rate of said foam includes the step of monitoring movement of a piston shaft with a linear voltage differential transformer or other measurement devices.

5. A process to generate a liquid-gas-surfactant foam as set forth in claim 1 wherein said step for controlling temperature of said fluids includes thermally insulating and heating said mixing cell.

6. A process to generate a liquid-gas-surfactant foam as set forth in claim 1 wherein said step of mixing said liquids and gases includes premixing said liquids prior to introduction to said mixing cell and then introducing said gases into said mixing cell.

7. A process to generate a liquid-gas-surfactant foam as set forth in claim 1 wherein said step of the use of view ports to enable visual observations and optical measurements of the physical properties of foam, including bubble size, size distribution and shape.

8. A process to generate a liquid-gas-surfactant foam as set forth in claim 1 wherein said step of pressurizing said mixing cell includes moving a piston within said mixing cell.

9. A process to generate a liquid-gas-surfactant foam as set forth in claim 1 wherein said step of mixing liquids and gases in said mixing cell includes a circulating pump in communication with said mixing cell.

10. A process to generate a liquid-gas-surfactant foam as set forth in claim 1 wherein the process of delivering foam from said mixing cell to a viscometer includes permitting flow of foam from said mixing cell and across to said viscometer at a constant pressure and temperature.

11. A process to generate a liquid-gas-surfactant foam as set forth in claim 1 wherein said step of mixing said liquids and gases to produce a foam includes rotating a propeller or impeller within said mixing cell.

12. A process to generate a liquid-gas-surfactant foam as set forth in claim 11 wherein the step of mixing includes shrouding said propeller or impeller.

13. A foam generator and viscometer apparatus which comprises:

a mixing cell for receiving liquid and gas;

a propeller to mix said liquid and gas fluids in said mixing cell in order to generate a foam;

a movable piston to vary volume in said mixing cell; and a viscometer in fluid communication with said mixing cell to evaluate rheology of said foam; and means to move said foam through said viscometer while evaluating said foam.

14. A foam generator and viscometer apparatus as set forth in claim 13 including a line between said mixing cell and viscometer, a line from said viscometer and view ports through said lines to enable visual observations or optical measurements of said foam.

15. A foam generator as set forth in claim 13 including a heater for said mixing cell to control temperature of said liquid and said gas.

16. A foam generator as set forth in claim 13 including means to measure and control rate of movement of said propeller.

17. A foam generator and viscometer as set forth in claim 13 wherein said moveable piston has recessed portions to enhance circulation within said mixing cell.

18. A foam generator and viscometer, as set forth in claim 13, including means to vary the surface roughness of the internal elements, including a stationary cup and a rotor or a stationary bob and a rotating sleeve in order to systematically study the effects of surface roughness on wall slip of a foam at solid boundaries.

19. A foam generator, as set forth in claim 13, including means to use a variety of propeller and/or impeller designs.

20. A foam generator as set forth in claim 14 wherein said mixing cell has a contoured geometry to promote flow within said mixing cell.

* * * * *